(12) United States Patent
Zografos et al.

(10) Patent No.: US 12,016,967 B2
(45) Date of Patent: *Jun. 25, 2024

(54) SANITATION MONITORING SYSTEM USING PATHOGEN SURROGATES AND SURROGATE TRACKING

(71) Applicant: SafeTraces, Inc., Pleasanton, CA (US)

(72) Inventors: Antonios Zografos, Oakland, CA (US); Laurie M. Clotilde, Hayward, CA (US); Peter Mattei, Lemon Grove, CA (US)

(73) Assignee: SafeTraces, Inc., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/486,767

(22) Filed: Sep. 27, 2021

(65) Prior Publication Data

US 2022/0080076 A1    Mar. 17, 2022

Related U.S. Application Data

(63) Continuation of application No. 16/741,668, filed on Jan. 13, 2020, now Pat. No. 11,129,915, which is a
(Continued)

(51) Int. Cl.
*A61L 2/28* (2006.01)
*G06T 11/60* (2006.01)
*G06T 19/00* (2011.01)

(52) U.S. Cl.
CPC ............... *A61L 2/28* (2013.01); *G06T 11/60* (2013.01); *G06T 19/006* (2013.01); *A61L 2202/14* (2013.01)

(58) Field of Classification Search
None
See application file for complete search history.

(56) References Cited

U.S. PATENT DOCUMENTS

| 1,913,069 A | 6/1933 | Chance |
| 4,593,360 A | 6/1986 | Cocks |

(Continued)

FOREIGN PATENT DOCUMENTS

| CN | 101379188 A | 3/2009 |
| CN | 104024426 A | 9/2014 |

(Continued)

OTHER PUBLICATIONS

Andrews, "DNA Spray-On Technology Could Revolutionize Food Traceability," Food Safety News, http://www.foodsafetynews.com/2014/11/dna-laced-spray-technology-could-revolutionize-food-traceability/#.W1kRNNVKjRY, Nov. 17, 2014, 2 pages.

(Continued)

*Primary Examiner* — Ryan M Gray
(74) *Attorney, Agent, or Firm* — Haynes and Boone, LLP

(57) ABSTRACT

A sanitation management system maintains records of exemplary locations on an item to be sanitized and indicates those locations to a person or system charged with applying a pathogen surrogate prior to a sanitation process. The sanitation management system maintains records of where the pathogen surrogate was applied prior to the sanitation process. Following the sanitation process, the sanitation management system indicates to an inspector, or an inspection system, locations of where the pathogen surrogate was applied for the purpose of facilitating testing of the sanitation process by checking for the presence of the pathogen surrogate at some or all of those locations. This can ensure that the inspection process is relevant to the sanitation process and less likely to generate false negatives where the inspection finds a lack of the pathogen surrogate not due to cleaning, but due to lack of application of the pathogen surrogate.

11 Claims, 9 Drawing Sheets

Stainless Steel Coupons Experiment

Related U.S. Application Data continuation of application No. 15/963,017, filed on Apr. 25, 2018, now Pat. No. 10,556,032.

(56) References Cited

U.S. PATENT DOCUMENTS

| | | | |
|---|---|---|---|
| 6,312,911 | B1 | 11/2001 | Bancroft et al. |
| 8,293,535 | B2 | 10/2012 | Farquar et al. |
| 10,556,032 | B2* | 2/2020 | Zografos ............... G06T 11/00 |
| 11,129,915 | B2* | 9/2021 | Zografos ............... G06T 19/006 |
| 2002/0129523 | A1 | 9/2002 | Hunt |
| 2004/0166520 | A1 | 8/2004 | Connolly |
| 2005/0031487 | A1 | 2/2005 | Rosenblatt et al. |
| 2006/0037222 | A1 | 2/2006 | Hunt et al. |
| 2006/0111845 | A1 | 5/2006 | Forbis et al. |
| 2009/0070134 | A1 | 3/2009 | Rodgers |
| 2010/0159434 | A1* | 6/2010 | Lampotang ............ G09B 23/28 434/365 |
| 2010/0261193 | A1 | 10/2010 | Webster et al. |
| 2011/0165569 | A1 | 7/2011 | Macula |
| 2011/0177539 | A1* | 7/2011 | Sutton .................... C12Q 1/485 435/8 |
| 2012/0112883 | A1 | 5/2012 | Wallace et al. |
| 2013/0052751 | A1 | 2/2013 | Farquar et al. |
| 2013/0122807 | A1 | 5/2013 | Tenarvitz et al. |
| 2014/0046722 | A1 | 2/2014 | Rosenbloom et al. |
| 2014/0057276 | A1 | 2/2014 | Farquar et al. |
| 2014/0108039 | A1 | 4/2014 | Rensvold et al. |
| 2014/0167917 | A2 | 6/2014 | Wallace et al. |
| 2014/0220576 | A1 | 8/2014 | Macula |
| 2014/0255984 | A1 | 9/2014 | Sharpin |
| 2014/0272097 | A1 | 9/2014 | Jung et al. |
| 2014/0340423 | A1 | 11/2014 | Taylor et al. |
| 2015/0034309 | A1 | 2/2015 | Blair |
| 2015/0205985 | A1 | 7/2015 | Jinadatha |
| 2015/0314026 | A1 | 11/2015 | Mauzerall et al. |
| 2015/0322426 | A1 | 11/2015 | Zografos et al. |
| 2015/0361490 | A1 | 12/2015 | Farquar et al. |
| 2016/0038083 | A1 | 2/2016 | Ding et al. |
| 2016/0102335 | A1* | 4/2016 | Franciskovich ............................ C12Y 302/01023 435/31 |
| 2016/0171179 | A1 | 6/2016 | Donofrio et al. |
| 2016/0188943 | A1 | 6/2016 | Franz |
| 2016/0306934 | A1 | 10/2016 | Sperry et al. |
| 2016/0307459 | A1 | 10/2016 | Chestnut et al. |
| 2017/0038353 | A1 | 2/2017 | Zografos et al. |
| 2017/0081707 | A1 | 3/2017 | Dillon et al. |
| 2017/0197002 | A1 | 7/2017 | Dobrinsky et al. |
| 2017/0322701 | A1 | 11/2017 | Bowman et al. |
| 2017/0333859 | A1 | 11/2017 | Lind |
| 2018/0108178 | A1* | 4/2018 | Murugappan ........... G01S 17/66 |
| 2018/0126021 | A1* | 5/2018 | Valentine ................. A61L 2/28 |
| 2018/0252738 | A1 | 9/2018 | Denney |
| 2018/0369438 | A1* | 12/2018 | Grossman ................ A61L 2/18 |
| 2019/0029002 | A1 | 1/2019 | Kotzer et al. |
| 2019/0086296 | A1* | 3/2019 | West ....................... G01N 21/94 |
| 2019/0087533 | A1 | 3/2019 | O'Hara |
| 2019/0120727 | A1 | 4/2019 | Harding et al. |
| 2019/0211324 | A1 | 7/2019 | Zografos et al. |
| 2019/0241982 | A1 | 8/2019 | Hogan et al. |
| 2019/0318807 | A1 | 10/2019 | O'Hara |

FOREIGN PATENT DOCUMENTS

| | | |
|---|---|---|
| CN | 104131008 A | 11/2014 |
| CN | 104513863 A | 4/2015 |
| WO | 2004063856 A2 | 7/2004 |
| WO | 2008137831 A1 | 11/2008 |
| WO | 2011163296 A2 | 12/2011 |
| WO | 2012037876 A1 | 3/2012 |
| WO | 2014164958 A1 | 10/2014 |
| WO | 2017049160 A2 | 3/2017 |
| WO | 2019157227 A1 | 8/2019 |

OTHER PUBLICATIONS

Busta et al., "The Use of Indicators and Surrogate Microorganisms for the Evaluation of Pathogens in Fresh and Fresh-Cut Produce," Comprehensive Reviews in Food Science and Food Safety, 2(s1), Jan. 2003, pp. 179-185.

Bystrykh, "Generalized DNA Barcode Design Based on Hamming Codes," Plos One 7(5):e36852, May 17, 2012, 8 pages.

Danyluk et al., "Process Validation: Selection and Use of Surrogates," University of Florida Institute of Food and Argicultural Sciences, presentation dated Apr. 2014, 19 pages.

Extended European Search Report dated Feb. 26, 2019, European Patent Application No. 16833458.9, filed Jun. 17, 2016, 5 pages.

Farquar, "DNATrax (DNA Tagged Reagents for Aerosol experiments)," Lawrence Livermore National Laboratory, presentation LLNL-PRES-642415, Aug. 2013, retrieved from the internet at http://web.archive.org/web/20160226230017/https://ipo.llnl.gov/technologies/individual-tech-discovery&p=DNATrax>, 6 pages.

Harding et al., "Unique DNA-barcoded aerosol test particles for studying aerosol transport," Aerosol Science and Technology 50(5):429-435, Mar. 22, 2016.

Hou et al., "Rapid bioparticle concentration and detection by combining a discharge driven vortex with surface enhanced Raman scattering," Biomicrofluids 1.014106:1-13, Feb. 16, 2007.

International Search Report and Written Opinion dated Aug. 8, 2019, International Patent Application No. PCT/US2019/029002, filed Apr. 24, 2019, 8 pages.

International Search Report and Written Opinion dated Sep. 8, 2016, International Patent Application No. PCT/US2016/038083, filed Jun. 17, 2016.

International Search Report and Written Opinion, dated Mar. 15, 2019, International Patent Applicaton No. PCT/US19/13069, filed Jan. 10, 2019, 13 pages.

Ma et al., "Development of Thermal Surrogate Microorganisms in Ground Beef for In-Plant Critical Control Point Validation Studies," Journal of Food Protection, 70(4), Apr. 2007, pp. 952-957.

Naaum, "Novel Methods of Species and Product Authenticity and Traceability Testing Using DNA Analysis for Food and Agricultural Applications," Doctoral Dissertation, Department of Integrative Biology University of Guelph, Apr. 2014, 144 pages.

Niebuhr et al., "Evaluation of non-pathogenic surrogate bacteria as process validation indicators for *Salmonella* enteric for selected antimicrobial treatments, cold storage and fermentation in meat," Journal of Food Protection, 71(4), Apr. 2008, pp. 714-718.

Oxford Gene Technology, "DNA Storage and Quality," Aug. 2011 [retrieved Oct. 30, 2018 https://www.ogt.com/resources/literature/403_dna_storage_and_quality, 5 pages.

Puddu et al., "Magnetically Recoverable, Thermostable, Hydrophobic DNA/Silica Encapsulates and Their Application as Invisible Oil Tags," ACS Nano 8(3):2677-2685, Feb. 25, 2014.

Sharma et al., "Hydrological Tracers Using Nanobiotechnology: Proof of Concept," Environmental Science and Technology, 46(16):8928-8936, Aug. 21, 2012.

Sinclair et al., "A Criteria for Selection of Surrogates Used to Study the Fate and Control of Pathogens in the Environment," Applied and Environmental Microbiology, 78(6), published online Jan. 13, 2012, published in print Mar. 2012, pp. 1969-1977.

Yeater et al., "Effectiveness of Sanitzing Products on Controlling Selected Pathogen Surrogates on Retail Dell Slicers," Journal of Food Protection, 78(4), Apr. 2015, pp. 707-715.

Ruther, "Assistive Systems for Quality Assurance by Context-aware User Interfaces in Health Care and Production," Diss. Universitatsbibliothek Bielefeld (2014).

European Search Report dated Oct. 20, 2020 issued in Application No. 19738614.7-1010/3566046 PCT/US2019013069, 8pages.

Galimberti et al., 'DNA barcoding for minor crops and food traceability' Advances in Agriculture, vol. 2014, Article ID.831875, internal pp. 1-8 (2014).

Galimberti et al., 'DNA barcoding as a new tool for food traceability' Food Research International, vol. 50, Issue.I, pp. 55-63 (2013).

International Search Report and Written Opinion dated Aug. 12, 2015, International Patent Application No. PCT/US2015/028880.

(56) References Cited

OTHER PUBLICATIONS

Extended European Search Report dated Jun. 15, 2018, European Patent Application No. 15878244.1.
International Search Report issued in PCT Application No. PCT/US2021/016065, dated May 24, 2021.
Kumar et al., "A rapid screening for adulterants in olive oil using DNA barcodes." Food Chemistry 127.3 (2011): 1335-1341 (Year: 2011), pp. 1336-1341.
Leier et al., "Cryptography with DNA binary strands." Biosystems 57 .1 (2000): 13-22. (Year: 2000), pp. 13-22.
Ovissipour et al., "DNA-based surrogate indicator for sanitation verification and predict inactivation of *Escherichia coli* O157:H7 using vibrational spectroscopy (FTIR)." Food Control 100 (2019): 67-77 (Year: 2019), pp. 67-77.
Singh et al., "DNA QR coding for data security using DNA sequence." International Journal of Information Technology 12.2 (Jan. 18, 2020): 571-576 (Year: 2020), pp. 571-576.
Vassou et al., "DNA barcoding for species identification from dried and powdered plant parts: A case study with authentication of the raw drug market samples of Sida cordifolia." Gene 559.1 (2015): 86-93 (Year:2015), pp. 86-93.
Yaari et al., "Theranostic barcoded nanoparticles for personalized cancer medicine." Nature communications 7.1 (2016): 13325 (Year: 2016), pp. 1-10.

\* cited by examiner

SANITATION MONITORING SYSTEM USING PATHOGEN SURROGATES AND SURROGATE TRACKING

CROSS-REFERENCES TO PRIORITY AND RELATED APPLICATIONS

This application claims priority from and is a continuation of non-provisional U.S. patent application Ser. No. 16/741,668, filed Jan. 13, 2020, which is a continuation of non-provisional U.S. patent application Ser. No. 15/963,017, filed Apr. 25, 2018, entitled "Sanitation Monitoring System Using Pathogen Surrogates and Surrogate Tracking." This application also incorporates by reference U.S. patent application Ser. No. 15/053,731, filed Feb. 25, 2016, now U.S. Pat. No. 10,556,032, issued Feb. 11, 2020, entitled "Pathogen Surrogates Based on Encapsulated Tagged DNA For Verification of Sanitation and Wash Water Systems for Fresh Produce" by Zografos, et al. (hereinafter "Zografos I").

FIELD OF THE INVENTION

The present disclosure generally relates to a sanitation monitoring system and/or sanitation practices. The disclosure relates more particularly to apparatus and techniques for applying pathogen surrogates, monitoring their application to surfaces to be sanitized, and by measuring pathogen surrogate presence post-sanitation, determining whether using sanitation was sufficiently performed.

The entire disclosure(s) of application(s)/patent(s) recited above is(are) hereby incorporated by reference, as if set forth in full in this document, for all purposes.

BACKGROUND

In many industries and situations, such as food production, medical facilities, and the like, sanitation is a critical portion of a workflow to produce a product or provide a service. For example, when food is produced on food processing equipment, it might be desirable to remove many harmful pathogens from the food processing equipment in advance. Harmful pathogens might not always be apparent upon visual inspection. One solution is to clean the equipment such that it is unlikely that harmful pathogens could survive. For example, a meat processing plant might subject a piece of equipment to a high temperature washing process that uses steam to kill any bacteria or viruses that might be present. However, for some equipment or spaces, high temperature washing processes might not be feasible, such as when cleaning large equipment, walls, floors, etc. Where the equipment and surfaces cannot be subjected to a cleaning that definitively heats all portions of the equipment or surfaces, another approach is needed.

Equipment and spaces can be cleaned by the application of cleaning substances, such as liquid cleaners, possibly using cleaning devices such as cloths, scrubbers, etc. To test for the efficacy of a cleaning process, one might sample test areas of the equipment and spaces for particular pathogens. This might miss pathogens on areas that are not tested for or some pathogens that are not tested for. One approach might be to apply pathogens onto the equipment and spaces then test for them after the sanitation process, but this can be hazardous as it introduces pathogens that might not be eliminated.

In one approach, harmless pathogen surrogates are used, such as methods described in Zografos I. In some of those approaches, an abiotic pathogen surrogate is applied to surfaces prior to a sanitation process, then the equipment and/or spaces are tested for the pathogen surrogate to determine whether the equipment and/or spaces were adequately sanitized. However, this can lead to false negatives. A pathogen surrogate might be applied to some, but not all, of a surface, the entire surface sanitized and then some part of the surface tested post-cleaning for the presence of the pathogen surrogate. Even when the surface was not adequately sanitized, it might still show sanitization if the portions upon which the pathogen surrogate was applied was not the portions used for testing. This also can be a problem if persons involved in the sanitation process limit their cleaning to only those portions known to be tagged with pathogen surrogates.

SUMMARY

In one embodiment, a sanitation management system maintains records of exemplary locations on an item to be sanitized, such as equipment, product, stock, spaces, or the like, and indicates some of those exemplary locations to a person or system charged with applying a pathogen surrogate prior to a sanitation process. The sanitation management system can also maintain records of where the pathogen surrogate was applied prior to the sanitation process. Following the sanitation process, the sanitation management system can indicate to an inspector, or an inspection system, the locations of where the pathogen surrogate was applied for the purpose of facilitating testing of the sanitation process by checking for the presence of the pathogen surrogate at some or all of those locations. This can ensure that the inspection process is relevant to the sanitation process and less likely to generate false negatives (i.e., cases where the inspection indicates that something lacks the pathogen surrogate and was therefore adequately cleaned, but in fact it lacked the pathogen surrogate in the first place).

The pathogen surrogate might comprise non-coding DNA sequences that form tags (or tag sequences) and a value can be encoded with tag sequences, such as where the presence of one tag sequence indicates a "1" in one binary position, the absence of that one tag sequence indicates a "0" in that binary position, and the set of presences and absences of tag sequences associated with various binary positions forms a binary word that provides information about the item in, or on, where the tag sequences are found. A taggant can comprise the tags and a carrier. For example, the carrier might be water, alcohol, wax, oil or some other base, such as a biofilm. In some embodiments, the taggant comprises a carrier that is a biofilm with characteristics selected to mimic the biological behavior of microorganisms that create natural biofilms.

Whether the pathogen surrogates use non-coding DNA sequences or there is some other method of distinguishing one pathogen surrogate from another pathogen surrogate, the use of coded pathogen surrogates can provide an indication of efficacy of a sanitation process that signals degrees of efficacy. For example, more than one pathogen surrogate might be applied where they have differing levels of resilience. By determining, from low resilience to high resilience, which pathogen surrogates were removed during the sanitation process, a measure of the efficacy of the sanitation process can be determined. For example, if five pathogen surrogates were applied, each with a distinct marker and each with a carrier that has a different resilience, a test following the sanitation process might provide for a value of 0 (all five pathogen surrogates appeared to be remaining after sanitation) to 4 (all the pathogen surrogates but the most resilient pathogen surrogate appeared to be removed) to 5 (all the pathogen surrogates appeared to be removed), etc.

The sanitation management system might maintain the records of exemplary locations on the item to be sanitized, records of where pathogen surrogate taggant was applied, and selected locations at which post-sanitation inspection testing is to be performed. These records might be stored in a computer system that is local or remote. The sanitation management system might further include augmented reality hardware, such as semi-transparent goggles smartphones and/or, that indicate, in situ, the application locations, where pathogen surrogate taggant is applied or was to be applied, and inspection locations, where a surface is to be tested for the presence of the pathogen surrogate taggant. Where the application locations are not disclosed to the person(s) or system(s) that are performing the sanitation, this can ensure that sanitation is complete and is not just a cleaning that is limited to the application locations.

The following detailed description together with the accompanying drawings will provide a better understanding of the nature and advantages of the present invention.

BRIEF DESCRIPTION OF THE DRAWINGS

Various embodiments in accordance with the present disclosure will be described with reference to the drawings, in which.

DETAILED DESCRIPTION

Figure 1:
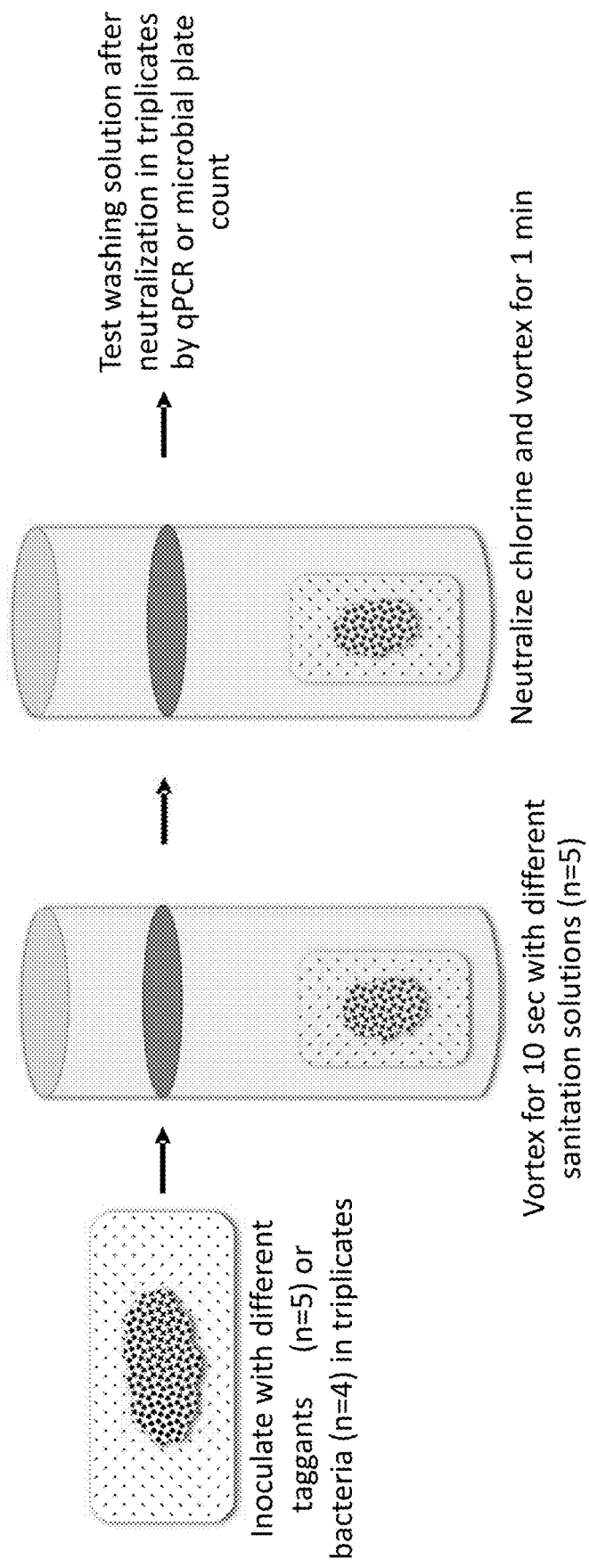
FIG. 1 shows an experimental process for evaluating taggants.

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

Techniques and apparatus described and suggested herein include a sanitation management system that maintains information about application and inspection for pathogen surrogates including pathogen surrogates using biofilms and augmented reality hardware to facilitate the application process and the inspection process. As used herein, the term "biofilm" might refer to a naturally occurring biofilm, such as one created by microorganisms in their typical environment. It might refer to something that is created naturally or synthetically to behave as a biofilm for various purposes, such as a biofilm simulant. It might also refer to an artificially created substance that acts as a biofilm. In any case, where the sanitation management system is used for food products, the biofilm might preferably be a food-grade material. Where the sanitation management system is used for other environments, such as cleaning surfaces needed for extreme vacuums, the biofilm might preferably be a material that does not outgas. Other environments might require other constraints on the biofilm (and possibly also the taggant used with the biofilm). Where needed, the biofilm can be made of edible, food-grade, food-safe, or "GRAS" (generally regarded as safe) materials. In some cases, such biofilms might be used on food-contacting surfaces while other biofilms are used elsewhere that are not expected to be in contact with food. In some cases, for simplicity or ease of implementation, all biofilms might be made from GRAS materials. Preferably, a sanitation system might use GRAS taggants, provide rapid results, be easy to use, be not detrimental to food quality, have behavior in the product and/or process similar to the pathogens being tested for, and be distinguishble from background microflora.

Problems in the food industry include sanitation assurance. For sanitation assurance, microbial tests on the finished products do not always guarantee lot quality. Testing of the equipment, environment, surfaces, etc. used can provide an indication of proper sanitation. By proxy and/or inference, the indication of proper sanitation might also be an indication of cleanliness of the product produced on the sanitized equipment. These techniques can be used as part of a process of sanitation and for monitoring compliance. For example, a company inspector or an outside inspector might place pathogen surrogates and biofilms on work surfaces and equipment prior to a company performing a sanitation process and then later the inspector can test for the presence of the pathogen surrogates and/or biofilms to score the sanitation process. This may lead to inspection ratings, inspection approvals, calls for improvements in processes, etc. as a result of the indication as recorded.

An example of a sanitation management system comprises a computer system, augmented reality hardware coupled to that computer system, access controls and storage for computer data, and can involve the use of taggants that serve as pathogen surrogates. A pathogen surrogate is a non-pathogen that can be applied to equipment, surfaces, etc. and can be cleaned off of equipment, a surface, etc. and its presence, lack of presence, concentration, etc. can be easily detected in an inspection process. An example taggant comprises a carrier, such as a biofilm or gelatin, and a tag material, such as non-encoding DNA sequences that are extracted from naturally occurring organisms or that are generated synthetically. The tag material can comprise a combination of DNA sequences or a set of DNA sequences wherein information is conveyable by the presence and/or absence of those DNA sequences.

In one example, the tag material contains a specific selection from among a set of N DNA sequences and the particular selection encodes for up to N bits of information. As an example, the set of N DNA sequences might be a set of 40 DNA sequences that are not found in nature and by mapping each bit of a 40-bit message to the presence or absence of one of those 40 DNA sequences, the 40-bit message can be conveyed by applying taggant having the corresponding selected set of those 40 DNA sequences. The presence and absence of the specific tags can be done by obtaining a portion of the taggant from the equipment, surface, etc. and applying a PCR process to extract the DNA patterns present in the taggant. In this manner, a "tag value"

comprising a 40-bit value (or some other value if greater than or less than 40 DNA sequences are used) can be read from a small sample.

In one specific example, the taggants comprise approximately 100 base pairs of DNA sequences from *Micromonas commode* and *Ostreococcus lucimarinus* that are non-coding, non-viable, non-toxic, and GRAS, encapsulated in food-grade materials that meet dietary requirements, such as being kosher, organic, non-GMO, halal and the like. The food-grade materials might be gums, resins, proteins, and/or lipids, such as carrageenan, albumin, soy lecithin, etc. The materials might have adjustable particle size and other adjustable properties.

In some uses, multiple taggants are applied with varying degrees of resilience. The tag values of taggants that are present can be read from a small sample and the relative concentrations of the different taggants can provide information about how well the set of taggants was removed. For example, M taggants might be applied, for some number M>1, each having some N-bit tag value, and a sanitation process performed. Then, in testing post-sanitation for the presence of taggants with the various tag values of pathogen surrogates that were applied, a degree of sanitation can be determined by noting the different tag values detected. In some cases, the varying degrees of resilience might be as to one sanitation process and/or one solvent, such as applying seven pathogen surrogates and having a degree of sanitation value that ranges from 0 (none of the seven were removed) to 7 (all of the seven were removed).

In other cases, the resilience might not be on a strictly linear scale. For example, some taggants might be resilient to one sanitation method, such as the application of heat, while others might be resilient to another sanitation method, such as the application of a cleaning solution. In such cases, there might be multiple sanitation efficacy metrics used together.

The taggant might include a gelatin biofilm, allowing the taggant to be applied to a particular surface. As used herein, the equipment, stock, product, surface, area, floor, wall, etc. to which a taggant serving as a pathogen surrogate is applied might be referred to as a "substrate." In a sanitation monitoring process, the taggant serving as a pathogen surrogate is applied to selected and identified places on a substrate prior to a sanitation process. Then, after a sanitation process is applied to the substrate and likely more portions of the equipment, stock, product, surface, area, floor, wall, etc., an inspector can return to the selected and identified places on the substrate and test for the presence of the taggant.

The inspection process might include determining ratios or relative presence, so as to be able to determine that some, a majority, but not all, of the applied taggant was removed during the sanitation process.

Surrogate Production

A pathogen surrogate includes a DNA bar code and a non-toxic pathogen surrogate carrier. The DNA bar code is combined with the surrogate carrier to form the pathogen surrogate, where the pathogen surrogate is degradable under a sanitation process.

The DNA sequences of the surrogates can be produced using bioinformatics, based on theoretical molecules, naturally-occurring DNA, or on an existing library of DNA sequences. The DNA portion of the pathogen surrogate can be produced chemically, synthetically using biotechnology, or via isolation/purification from natural sources.

The robustness of the DNA carrier material can define the resistance of the surrogate to the sanitizing agent. For example, a pathogen surrogate that is easy to destroy via sanitization can be developed, based on a DNA tagged biosimulant for aerosol transport studies. The formulation can be a maltodextrin carrier and be water-soluble. The solubility of the material makes the DNA readily available to any oxidative sanitizer, such as active chlorine, if the material is in a water environment. This allows for a very basic but significant check for cleaning procedures.

A PLGA-based carrier can also be used. PLGAs are biodegradable copolymers of poly(lactic-co-glycolic acid) and they decompose through hydrolysis, which is accelerated at elevated pH and oxidative conditions. PLGA hydrolysis rates are also dependent on ratios of lactic acid and glycolic acid. With this dependence, degradation rates of the pathogen surrogate can match a target pathogen. The surface of PLGA is relatively hydrophobic and may associate with surfaces non-specifically. PLGA also bears pendant carboxylic acid groups, which may be chemically modified to introduce a relatively low density of functional ligands.

In other embodiments, a surrogate can be produced from a gelatin-based carrier. Gelatin has many unique properties, most notably very low solubility in cold water and high solubility in hot water. Because it is a protein, gelatin provides a particle surface bearing primary amine and carboxyl chemical moieties, which are easily modified via controllable chemical reactions, producing a relatively high density of ligands. Other temperature-dependent surrogates may also be used. Other examples of surrogate carrier can include: carrageenan, carnauba, silica, water-soluble carbohydrate, flour, albumin, casein, a particle bearing a core of a functionally ferromagnetic material, or carrier using fixed (killed) cells of a formerly living microorganism.

In an overall process, the computer system might include a model of the equipment or where the substrates might be present. For example, for a machine that feeds raw food into an oven pipeline, the surfaces of the tables and rollers that roll the raw food into the oven might be more in need of sanitation practices for microbe elimination than the interior of the oven. The sanitation system can begin with an application process. In this step, a supervisor or other person might wear an augmented reality headset. The augmented reality headset would allow the user to see the physical surroundings, but overlays that with computer-generated imagery that appears to the user to be imagery statically placed in the physical surroundings even as the headset moves. The headset might be connected to the computer system wirelessly. In an example operation, the computer system will consider the model of the equipment, determine that a specific location on a tray should be a recipient of taggant and will convey that information to the headset. The headset might then display a marker, such as a dot, line, box, circle, or highlight to indicate to the wearer that taggant should be applied where the marker so indicates. The wearer would then apply the taggant as indicated and provide feedback so that the computer system can record that the wearer did in fact apply the taggant.

The taggant might be applied using a spray, brush or other application device. In one example, the wearer of the headset carries a pressurized aerosol can and sprays where indicated and presses a button to indicate that act. The computer system might then send the headset an indication of the next location on a substrate to apply the taggant. The augmented reality system might be able to automatically determine, by cameras or other apparatus, that the wearer did apply the taggant, such as by detecting the image of taggant being sprayed and comparing that to the location the computer indicated to be the substrate target position.

In one variation, some predetermined locations are marked with RFID chips so that a combination of an RFID reader and the A/R hardware can be used to direct the user to where to apply the taggants and where to later return for testing. This may allow a more precise application of the tags. This would also be useful in identifying locations to return to during the sanitation process, as would be the case with equipment having moving parts, such as belts, rollers, brushes, etc.

With this augmented reality system and headset, a wearer could quickly apply taggant to many different locations as specified by the computer system. The computer system can track those locations and which ones the wearer actually applied taggant.

Following the application process, a sanitation process can occur. The sanitation process can be a conventional sanitation process and can be performed by someone or a team of people who are unaware of where the taggant was applied, or even unaware that taggant was applied. Being unaware of where the taggant was applied, those persons would not be able to short-cut the sanitation process to only clean those portions of substrates where the taggant was applied.

Following the sanitation process, an inspection process is performed. An inspector wears an augmented reality system and headset, perhaps the same as was used in the application process. The computer system conveys to the headset particular locations on a substrate corresponding to where the computer system recorded taggant being applied in the application step. The inspector then takes a sample and indicates sampling is complete, and then the headset displays another sampling location. In this manner, the inspector can quickly sample substrates where taggant was applied and skip over substrates where no taggant was applied.

The collected samples can then be supplied to a measuring system, which might also be coupled to the computer system to provide measurements of how much taggant was sampled, also perhaps including some quantitative measure of how much was removed in the sanitation process.

Example

In a specific example of a sanitation management system, abiotic pathogen surrogates are used to monitor and/or characterize a sanitation process. Sanitation and environmental monitoring is important in many instances. Microbial testing is simple and inexpensive, but is not often sensitive enough and the turn-around time (from sample gathering to test results) can be too long. ATP (adenosine triphosphate) sanitation monitoring systems might be used, which detect and measure ATP on surfaces and in liquids as a method of determining the relative cleanliness of the surface or liquid. A downside is that ATP testing is sensitive to physical and chemical conditions and often is uncorrelated with bacterial counts. Microbial tests do not guarantee safety, create sampling challenges, and often involve non-uniform manufacturing conditions, non-uniform distribution of contamination, and non-uniform sampling. Slow test processes can drive up waste and inventory costs. These can create problems for the food processing industry.

Environmental monitoring might require varying levels, such as testing on food-contact surfaces, which is more critical than adjacent non-food contact surfaces, surfaces nearby and surfaces outside a processing space. Each of these might be found in need of testing however.

According to one embodiment, the techniques described herein are implemented by one or more generalized computing systems programmed to perform the techniques pursuant to program instructions in firmware, memory, other storage, or a combination. Special-purpose computing devices may be used, such as desktop computer systems, portable computer systems, handheld devices, networking devices or any other device that incorporates hard-wired and/or program logic to implement the techniques.

Testing

In an experiment to test how taggants and sanitation might work, a steel plate was prepared with five taggants and another steel place with four bacterial samples, and this experiment was repeated. The experimental process, as illustrated in FIG. 1, involved placing the steel plate into a vortex for 10 seconds with various sanitation liquids, then neutralizing with chlorine in a vortex for one minute. Then, the washing solution is tested after neutralization in triplicates by qPCR or microbial plate count.

Figure 2:
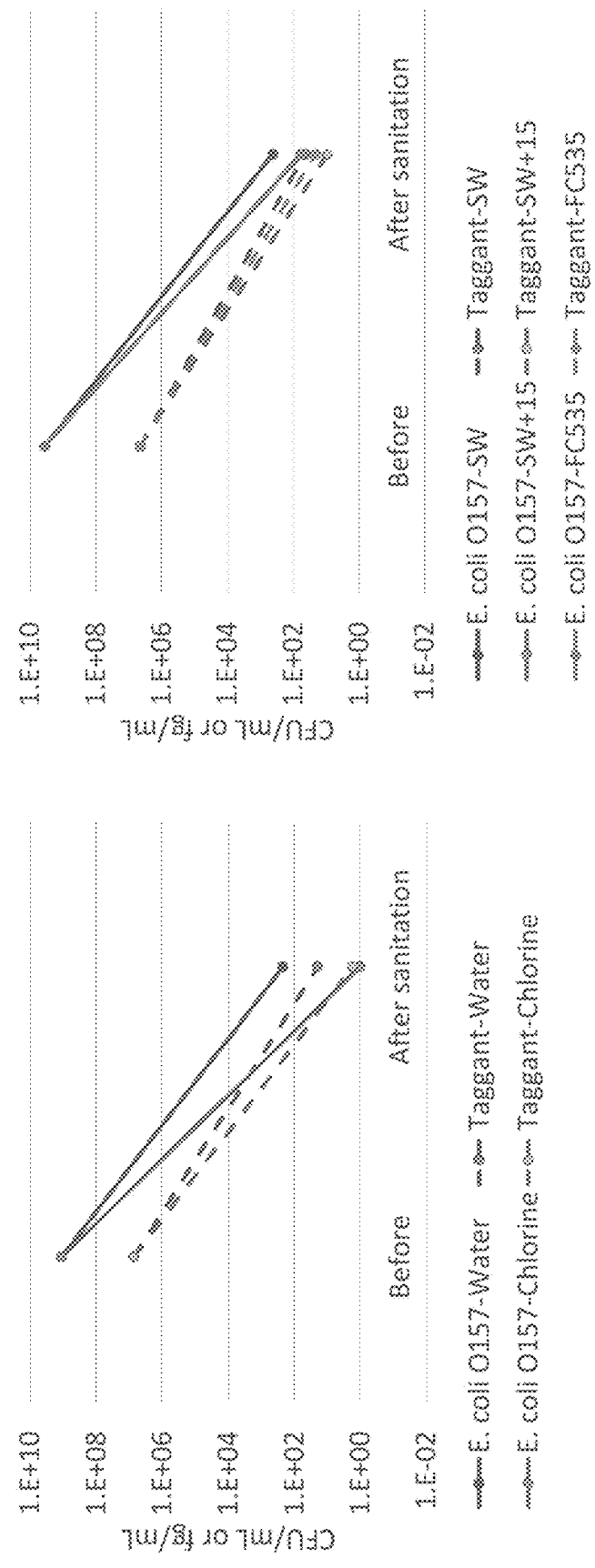
FIG. 2 shows test results and correlation for taggants and *E. coli* O157.

FIG. 2 shows test results and correlation for taggants and *E. coli* O157.

Figure 3:
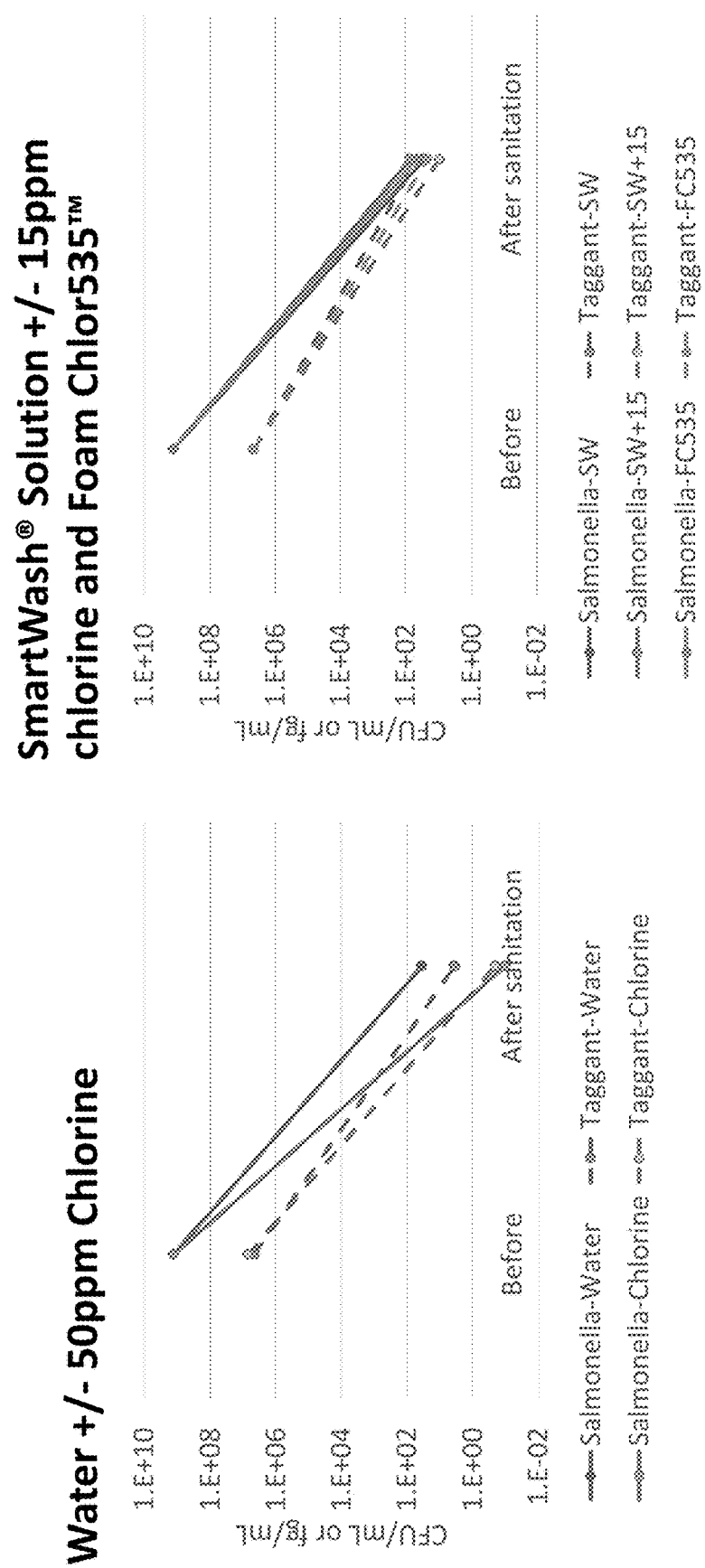
FIG. 3 shows test results and correlation for taggants and *Salmonella*.

FIG. 3 shows test results and correlation for taggants and *Salmonella*.

Figure 4:
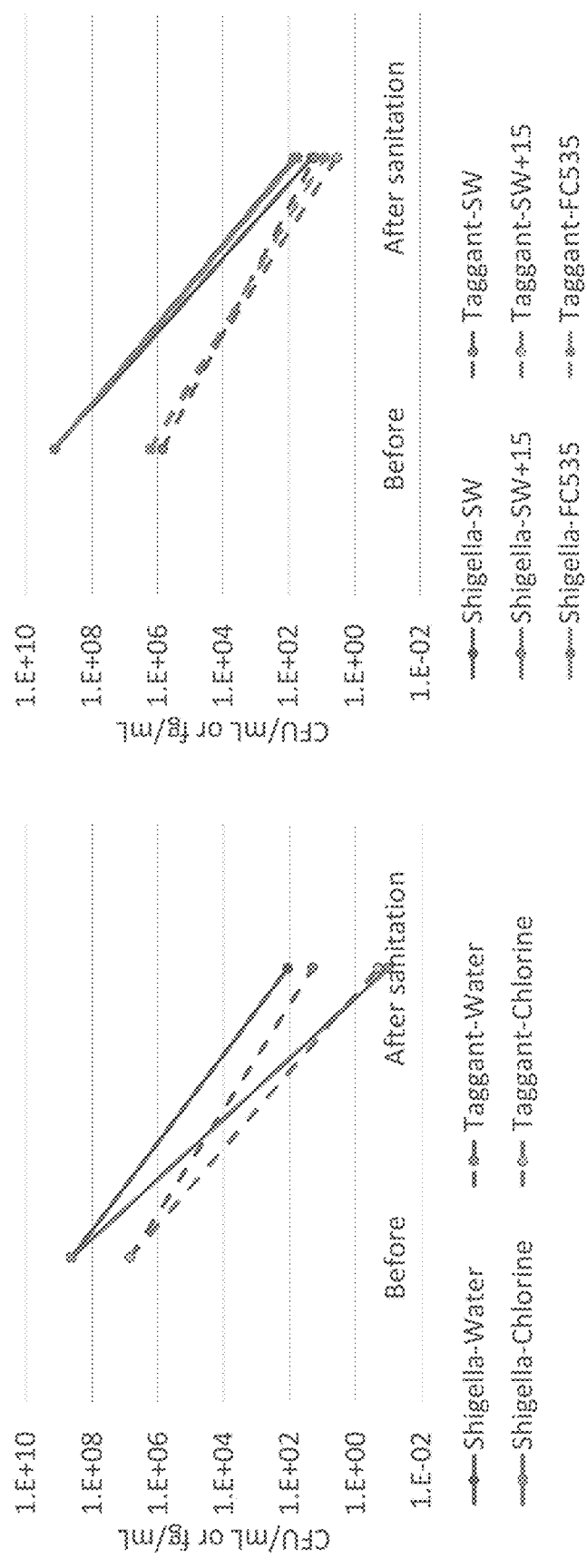
FIG. 4 shows test results and correlation for taggants and *Shigella*.

FIG. 4 shows test results and correlation for taggants and *Shigella*.

Figure 5:
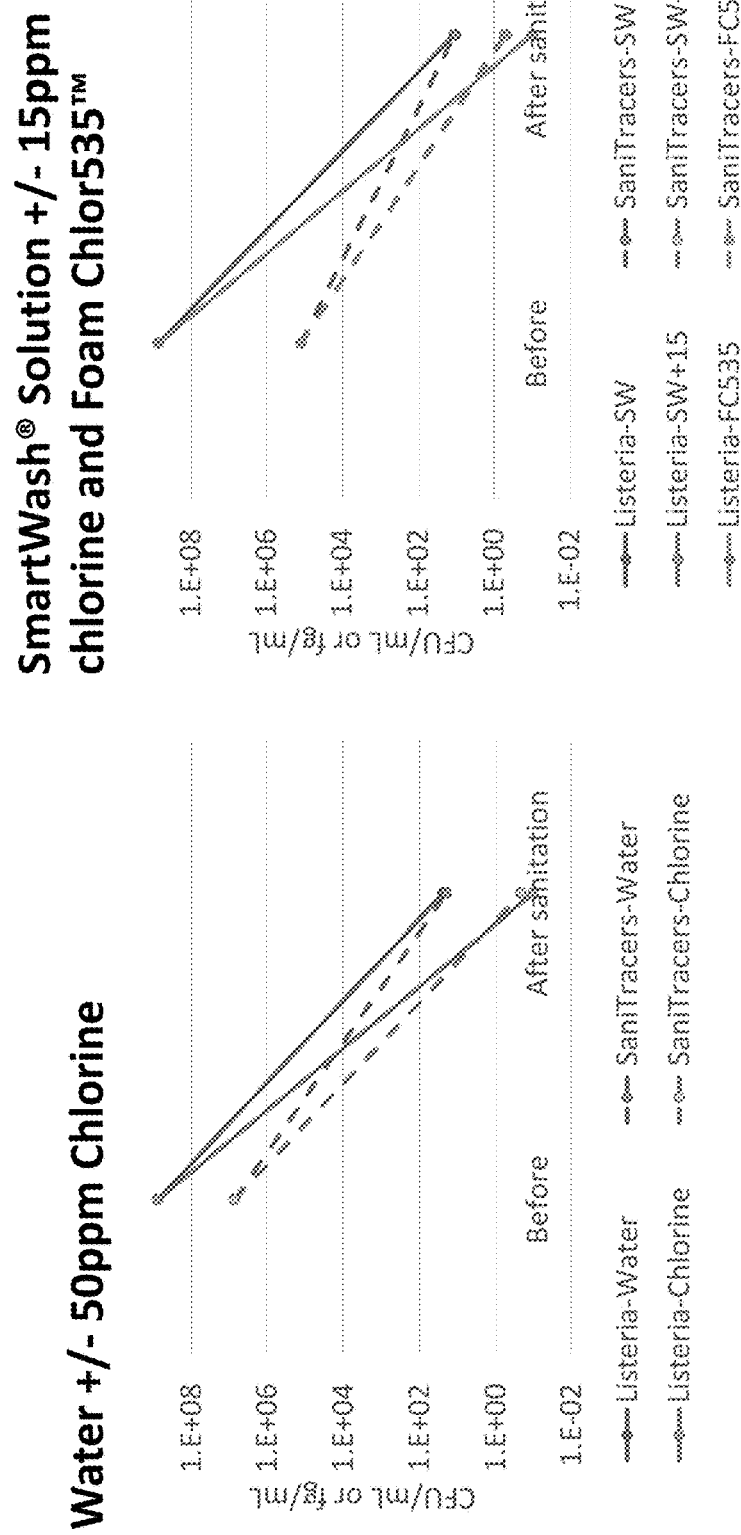
FIG. 5 shows test results and correlation for taggants and *Listeria*.

FIG. 5 shows test results and correlation for taggants and *Listeria*.

Figure 6:
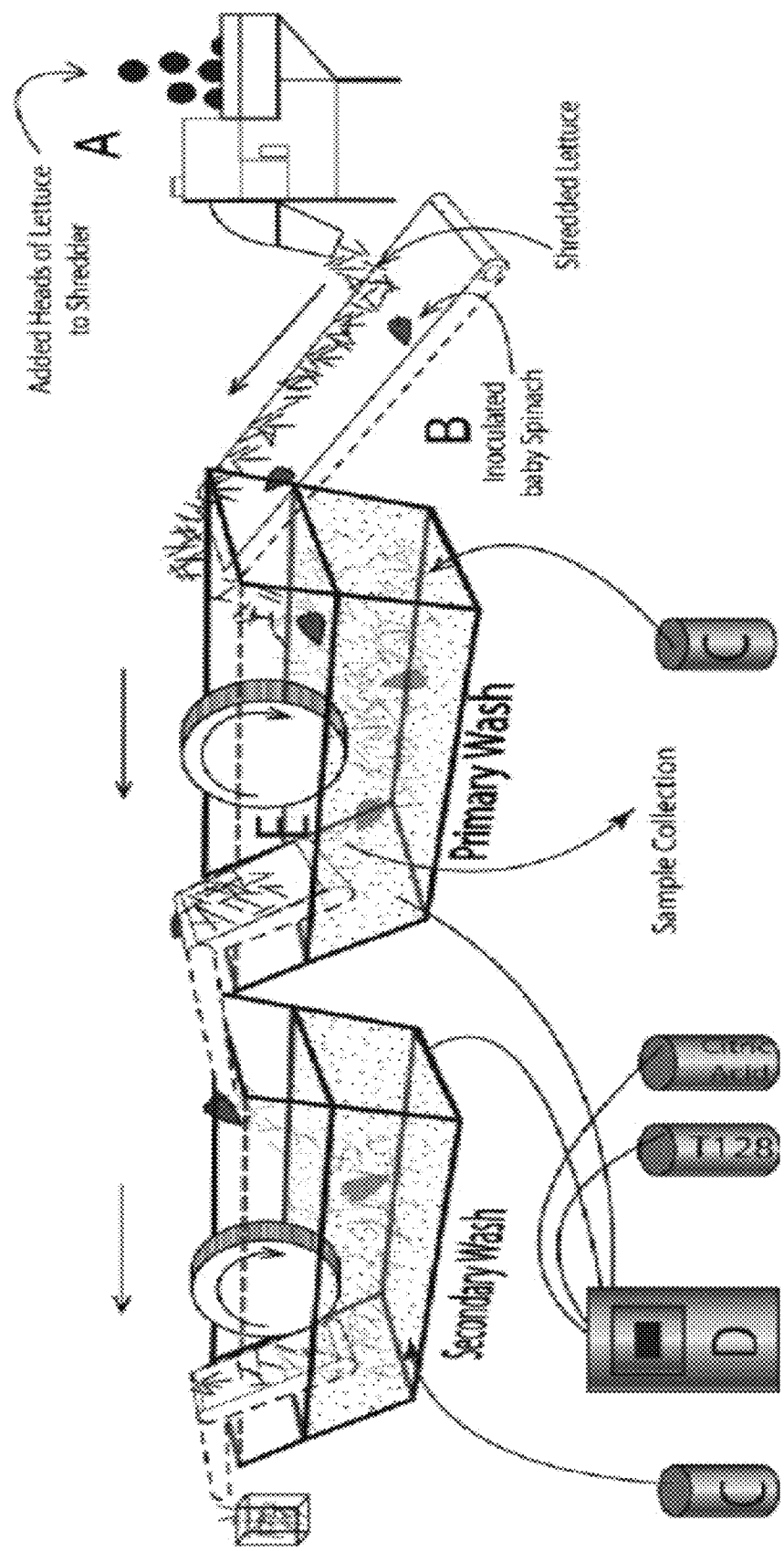
FIG. 6 illustrates an example of a produce wash flume system in which taggants might be used.

FIG. 6 illustrates an example of a produce wash flume system in which taggants might be used. As shown there, the lettuce is tagged with taggant (or a separate type of lettuce is tagged, such as baby spinach inserted with shredded head lettuce). This passes through a primary wash, is quickly tested, then proceeds through a second wash and can be tested again.

Figure 7:
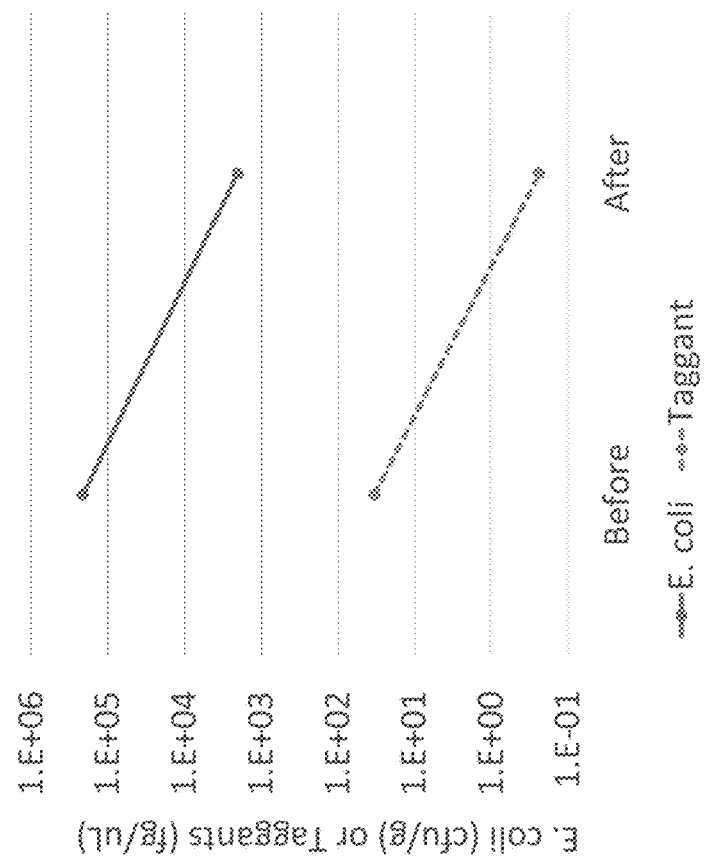
FIG. 7 shows test results and correlation for taggants and *E. coli* O157 in a produce wash flume system.

FIG. 7 shows test results and correlation for taggants and *E. coli* O157 in a produce wash flume system.

Figure 8:
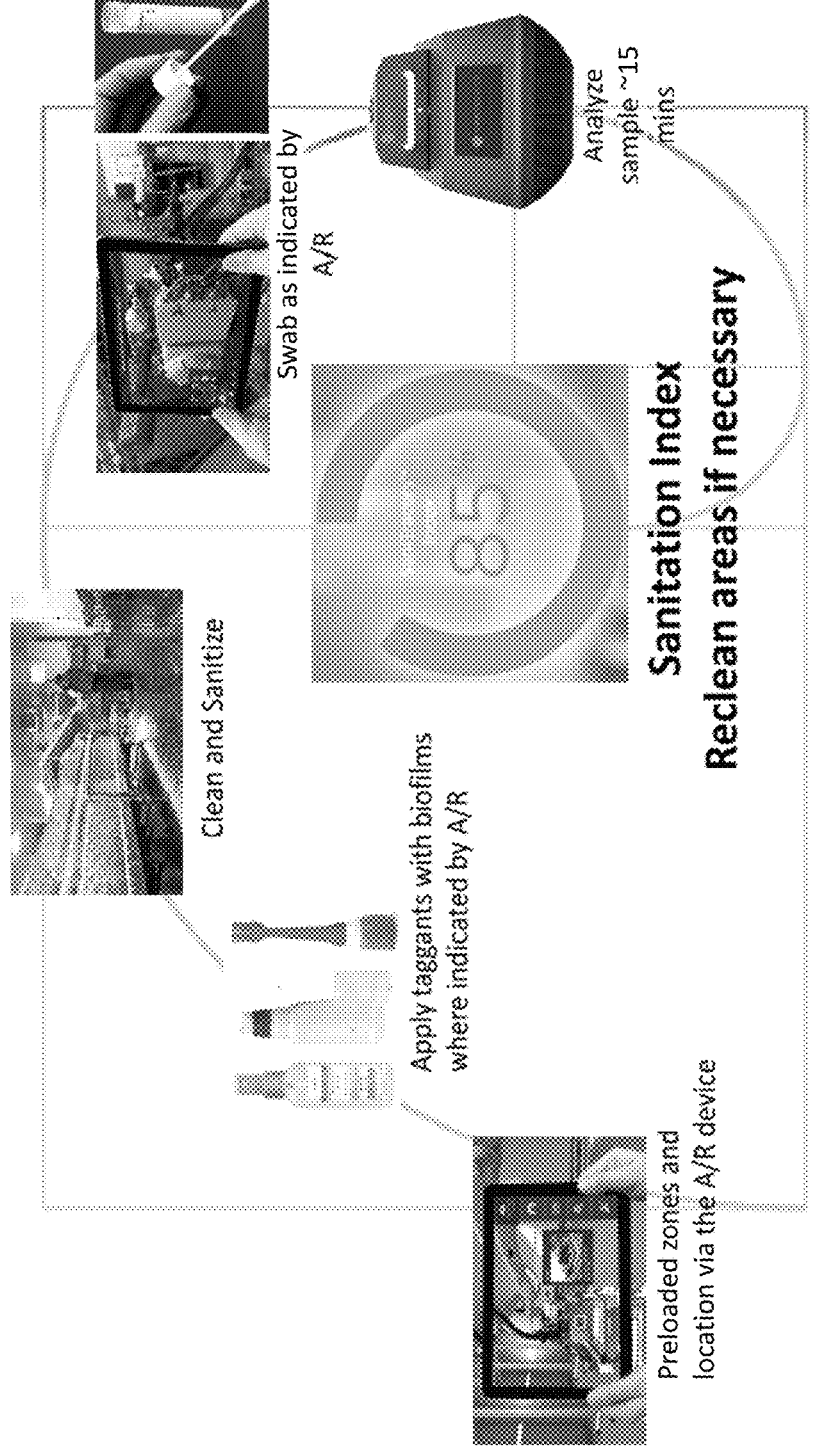
FIG. 8 illustrates a process of equipment and facility sanitation.

FIG. 8 illustrates a process of equipment and facility sanitation. As illustrated, a tablet computer or other A/R hardware shows preloaded zones and locations. A tester can apply the taggants/biofilms where indicated by the A/R hardware. Then, the equipment is cleaned and sanitized. The A/R hardware can then be used to indicate where to swab to obtain samples. Those samples can then be analyzed and a score provided.

Hardware

Figure 9:
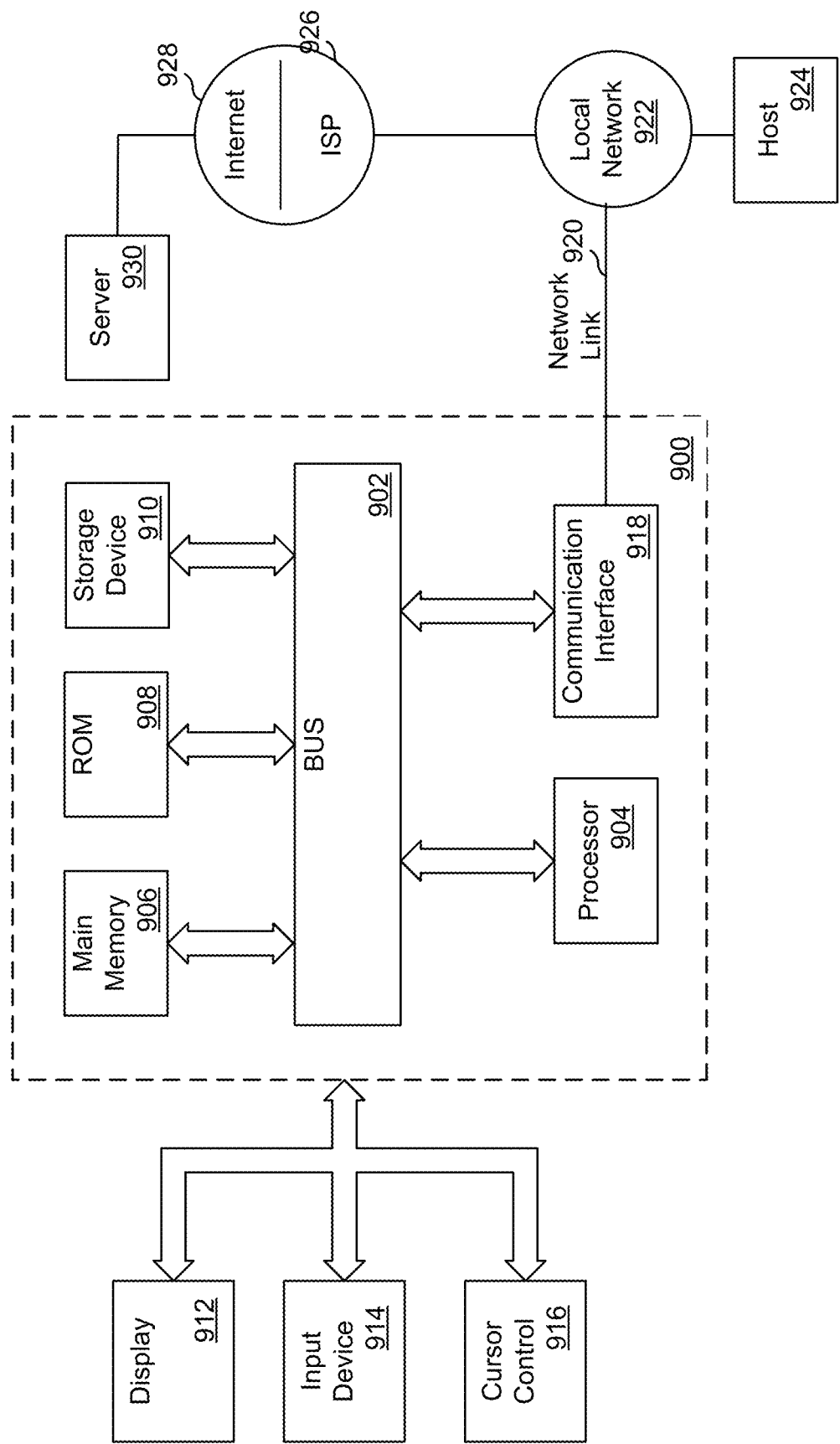
FIG. 9 is a block diagram that illustrates a computer system upon which an embodiment might be implemented.

FIG. 9 is a block diagram that illustrates a computer system 900 upon which an embodiment of the invention may be implemented. Computer system 900 includes a bus 902 or other communication mechanism for communicating information, and a processor 904 coupled with bus 902 for processing information. Processor 904 may be, for example, a general purpose microprocessor.

Computer system 900 also includes a main memory 906, such as a random access memory (RAM) or other dynamic storage device, coupled to bus 902 for storing information and instructions to be executed by processor 904. Main memory 906 also may be used for storing temporary variables or other intermediate information during execution of instructions to be executed by processor 904. Such instructions, when stored in non-transitory storage media accessible to processor 904, render computer system 900 into a special-purpose machine that is customized to perform the operations specified in the instructions.

Computer system 900 further includes a read only memory (ROM) 908 or other static storage device coupled to bus 902 for storing static information and instructions for processor 904. A storage device 910, such as a magnetic disk or optical disk, is provided and coupled to bus 902 for storing information and instructions.

Computer system 900 may be coupled via bus 902 to a display 912, such as a computer monitor, for displaying information to a computer user. An input device 914, including alphanumeric and other keys, is coupled to bus 902 for communicating information and command selections to processor 904. Another type of user input device is cursor control 916, such as a mouse, a trackball, or cursor direction keys for communicating direction information and command selections to processor 904 and for controlling cursor movement on display 912. This input device typically has two degrees of freedom in two axes, a first axis (e.g., x) and a second axis (e.g., y), that allows the device to specify positions in a plane.

Computer system 900 may implement the techniques described herein using customized hard-wired logic, one or more ASICs or FPGAs, firmware and/or program logic which in combination with the computer system causes or programs computer system 900 to be a special-purpose machine. According to one embodiment, the techniques herein are performed by computer system 900 in response to processor 904 executing one or more sequences of one or more instructions contained in main memory 906. Such instructions may be read into main memory 906 from another storage medium, such as storage device 910. Execution of the sequences of instructions contained in main memory 906 causes processor 904 to perform the process steps described herein. In alternative embodiments, hard-wired circuitry may be used in place of or in combination with software instructions.

The term "storage media" as used herein refers to any non-transitory media that store data and/or instructions that cause a machine to operation in a specific fashion. Such storage media may comprise non-volatile media and/or volatile media. Non-volatile media includes, for example, optical or magnetic disks, such as storage device 910. Volatile media includes dynamic memory, such as main memory 906. Common forms of storage media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, an EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus 902. Transmission media can also take the form of acoustic or light waves, such as those generated during radio-wave and infra-red data communications.

Various forms of media may be involved in carrying one or more sequences of one or more instructions to processor 904 for execution. For example, the instructions may initially be carried on a magnetic disk or solid state drive of a remote computer. The remote computer can load the instructions into its dynamic memory and send the instructions over a network connection. A modem or network interface local to computer system 900 can receive the data. Bus 902 carries the data to main memory 906, from which processor 904 retrieves and executes the instructions. The instructions received by main memory 906 may optionally be stored on storage device 910 either before or after execution by processor 904.

Computer system 900 also includes a communication interface 918 coupled to bus 902. Communication interface 918 provides a two-way data communication coupling to a network link 920 that is connected to a local network 922. For example, communication interface 918 may be an integrated services digital network (ISDN) card, cable modem, satellite modem, or a modem to provide a data communication connection to a corresponding type of telephone line. Wireless links may also be implemented. In any such implementation, communication interface 918 sends and receives electrical, electromagnetic or optical signals that carry digital data streams representing various types of information.

Network link 920 typically provides data communication through one or more networks to other data devices. For example, network link 920 may provide a connection through local network 922 to a host computer 924 or to data equipment operated by an Internet Service Provider (ISP) 926. ISP 926 in turn provides data communication services through the worldwide packet data communication network now commonly referred to as the "Internet" 928. Local network 922 and Internet 928 both use electrical, electromagnetic, or optical signals that carry digital data streams. The signals through the various networks and the signals on network link 920 and through communication interface 918, which carry the digital data to and from computer system 900, are example forms of transmission media.

Computer system 900 can send messages and receive data, including program code, through the network(s), network link 920 and communication interface 918. In the Internet example, a server 930 might transmit a requested code for an application program through Internet 928, ISP 926, local network 922 and communication interface 918. The received code may be executed by processor 904 as it is received, and/or stored in storage device 910, or other non-volatile storage for later execution.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

In the foregoing specification, embodiments of the invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction.

Further embodiments can be envisioned to one of ordinary skill in the art after reading this disclosure. In other embodiments, combinations or sub-combinations of the above-disclosed invention can be advantageously made. The example arrangements of components are shown for purposes of illustration and it should be understood that combinations, additions, re-arrangements, and the like are contemplated in alternative embodiments of the present invention. Thus, while the invention has been described with respect to exemplary embodiments, one skilled in the art will recognize that numerous modifications are possible.

For example, the processes described herein may be implemented using hardware components, software components, and/or any combination thereof. The specification and drawings are, accordingly, to be regarded in an illustrative rather than a restrictive sense. It will, however, be evident that various modifications and changes may be made thereunto without departing from the broader spirit and scope of the invention as set forth in the claims and that the invention is intended to cover all modifications and equivalents within the scope of the following claims.

All references, including publications, patent applications, and patents, cited herein are hereby incorporated by reference to the same extent as if each reference were individually and specifically indicated to be incorporated by reference and were set forth in its entirety herein.

What is claimed is:

1. A sanitation management system comprising:
   a computer capable of maintaining records of exemplary locations on an item to be sanitized and records of where a pathogen surrogate was applied prior to a sanitation process, the pathogen surrogate comprising a carrier that mimics biological behavior of pathogens that create biofilms;
   an augmented reality display that can display marks corresponding to the exemplary locations undergoing sanitation;
   an interface to gather information about how the pathogen surrogate was applied to the exemplary locations; and
   an inspection interface to provide, via the augmented reality display, sampling locations at which to check for presence of the pathogen surrogate at some or all of the exemplary locations.

2. The sanitation management system of claim 1, wherein the pathogen surrogate comprises non-coding DNA sequences that form tags or tag sequences.

3. The sanitation management system of claim 2, wherein the pathogen surrogate comprises tags, or tag sequences, and the carrier.

4. The sanitation management system of claim 3, wherein the carrier comprises one or more of water, alcohol, wax, oil, or other base.

5. The sanitation management system of claim 4, wherein the carrier comprises a carrier biofilm and the carrier biofilm has characteristics selected to mimic biological behavior of microorganisms that create natural biofilms.

6. The sanitation management system of claim 1, further comprising wireless communication components.

7. The sanitation management system of claim 1, wherein the pathogen surrogate comprises a tag bound to the carrier, wherein the tag comprises a DNA sequence corresponding to an N-bit tag value, and wherein the carrier is non-toxic.

8. The sanitation management system of claim 1, wherein the carrier is a PLGA-based carrier comprising a biodegradable copolymer of poly(lactic-co-glycolic acid) having a determined PLGA hydrolysis rate dependent on a ratio of lactic acid to glycolic acid used, whereby a degradation rate of the pathogen surrogate is aligned with a target pathogen.

9. The sanitation management system of claim 1, wherein the records of where the pathogen surrogate was applied comprises records for a plurality of pathogen surrogates that are applied, the plurality of pathogen surrogates comprising at least a first pathogen surrogate comprising a first carrier and a second pathogen surrogate comprising a second carrier, wherein the first carrier has a first level of resilience to the sanitation process and the second carrier has a second level of resilience to the sanitation process, whereby a low resilience carrier is more easily removed during the sanitation process as compared to a high resilience carrier, to provide an indication of a degree of sanitation.

10. The sanitation management system of claim 9, wherein each pathogen surrogate of the plurality of pathogen surrogates is applied with an associated degree of resilience, and the sanitation management system further comprises a sampler for reading relative concentrations of the plurality of pathogen surrogates following the sanitation process.

11. The sanitation management system of claim 10, wherein each pathogen surrogate further comprises a plurality of tags, each bound to a particular carrier characterized by a degree of resilience, whereby the degree of sanitation is determined based on which of the plurality of tags are found in that the sampling locations.

* * * * *

UNITED STATES PATENT AND TRADEMARK OFFICE
CERTIFICATE OF CORRECTION

| | | |
|---|---|---|
| PATENT NO. | : 12,016,967 B2 | Page 1 of 1 |
| APPLICATION NO. | : 17/486767 | |
| DATED | : June 25, 2024 | |
| INVENTOR(S) | : Antonios Zografos, Laurie M. Clotilde and Peter Mattei | |

It is certified that error appears in the above-identified patent and that said Letters Patent is hereby corrected as shown below:

In the Specification

Column 1, Line 16, change "Pat. No. 10,556,032, issued Feb. 11, 2020" to --Pat. No. 10,962,512, issued Mar. 30 2021--

Signed and Sealed this
First Day of July, 2025

Coke Morgan Stewart
*Acting Director of the United States Patent and Trademark Office*